United States Patent [19]

Kato et al.

[11]  4,411,793

[45]  Oct. 25, 1983

[54] PROCESS FOR THE SEPARATION OF ELEMENTS BY CHROMATOGRAPHY

[75] Inventors: Michio Kato; Toshiyuki Endo; Junji Nomura, all of Fuji, Japan

[73] Assignee: Asahi Kasei Kogyo Kabushiki Kaisha, Osaka, Japan

[21] Appl. No.: 333,696

[22] Filed: Dec. 23, 1981

[30] Foreign Application Priority Data

Dec. 24, 1980 [JP] Japan .............................. 55-181833
Dec. 27, 1980 [JP] Japan .............................. 55-185088

[51] Int. Cl.$^3$ ............................................. B01D 15/08
[52] U.S. Cl. ........................................ 210/656; 55/67
[58] Field of Search ............... 210/635, 656, 674, 686; 55/67

[56] References Cited

U.S. PATENT DOCUMENTS 2,487,574 11/1949 Meng ................................. 210/656
2,798,789 7/1957 Spedding et al. ............... 210/674 X
3,167,389 1/1965 Woyski ........................... 210/681 X
3,228,750 1/1966 Lindstrom et al. ............. 210/681 X
4,042,327 8/1977 Hanep et al. ........................ 210/656

Primary Examiner—John Adee
Attorney, Agent, or Firm—Birch, Stewart, Kolasch & Birch

[57] ABSTRACT

In a process for the separation of elements by chromatography in which a front zone and a rear zone are present in front of and in rear of an adsorption band of elements, a high column efficiency can be attained by developing the adsorption band of elements without causing the entry of a main eluent having a relatively high concentration into the front zone. According to the present invention, elements can be separated into individual species not only in a high state of purity but also in a high state of concentration, so that the productivity of elements may be extremely increased as compared with that of conventional methods. In addition, according to the present invention, the amount of eluent employed is remarkably small as compared with that in conventional methods. Therefore, the present invention is very advantageous for the separation of elements from an industrial standpoint.

21 Claims, No Drawings

PROCESS FOR THE SEPARATION OF ELEMENTS BY CHROMATOGRAPHY

This invention relates to a process for the separation of elements by chromatography. More particularly, the present invention is concerned with a process for the separation of elements by chromatography in which a front zone and a rear zone are present in front of and in rear of an adsorption band of elements to be separated, respectively, which comprises developing the adsorption band formed on the adsorbent packed in a column without causing the entry of a developing solution having a relatively high concentration (hereinafter referred to as "main eluent") into the front zone.

As one of the most useful methods for the separation of mixtures and for the purification of the substances, chromatography, particularly the so-called displacement chromatography, is known in which a front zone and a rear zone are present in front of and in rear of an adsorption band of substances to be separated, respectively. In this conventional chromatography, the adsorption band of substances formed on the adsorbent packed in a column is commonly developed while allowing an eluent to enter into the front zone which is present in front of the adsorption band. In such a method, disadvantageous phenomena such as reaction, precipitation and accumulation of the eluent tend to occur during the development of the adsorption band. To remove such phenomena, the separation of mixtures by chromatography has been carried out under extremely restrained development conditions.

For example, in the U.S. Pat. Nos. 2,798,789 and 3,228,750, there is disclosed a process for the separation of rare earth elements by chromatography which comprises adsorbing a mixture of rare earth elements on an ion exchanger packed in a column until the length of the adsorption band of the mixture reaches one-third the entire length of the ion exchanger and developing the formed adsorption band using a developing solution having an average concentration as low as 15 mmol/liter. While this method yields very pure individual rare earth species, it does have several disadvantages. The first disadvantage is that not only is the amount of rare earth elements which can be separated small but, also, a large amount of ligand solution is required to separate a rare earth mixture. This is so because the adsorbing capacity of the conventially known ion exchanger for rare earth elements is poor and hence a long developing bed having a length of 3 to 10 times the length of the adsorption band of a rare earth mixture is needed. When this method is carried out on a commercial scale, the operation is complicated because of necessity of the long ion exchanger column, and, in addition, extremely large capacity tanks for a ligand solution and an eluate are required. The second disadvantage of the method is that the concentration of elements in the eluate is extremely low. The eluate contains an element in a concentration of only about 15 mmol/liter. This is the most serious disadvantage in this method. In this method, since the concentrations of elements in the eluate are extremely low, the formation of precipitates for recovering elements from the obtained eluate and the filtration of the resulting precipitates cannot be efficiently achieved. Because of the above-mentioned disadvantages, this method has not been regarded as an advantageous method from the standpoint of industry.

As a method for increasing the concentration of separated elements in the eluate, increasing the concentration of a ligand solution employed as an eluent is considered to be effective. However, the concentration of the ligand employed is restrained by its solubility.

Illustratively stated, for example, when ethylenediaminetetraacetic acid (hereinafter referred to as "EDTA") is used as a ligand, a 6H-EDTA band is formed in the front zone after EDTA in a $NH_4$ form passes through an adsorption band of a rare earth mixture and the solubility of the resulting 6H-EDTA is lowered due to a low pH value of the liquid which is present in the front zone, so that the concentration of EDTA employed as an eluent is restrained by the solubility of 6H-EDTA in the front zone. Therefore, in the case where a ligand solution having a concentration exceeding a certain limit is employed, the ligand precipitates in the ion exchange column and clogging occurs inside the column, so that it becomes difficult to separate substances. For this reason, there has conventionally been used an eluent containing a ligand in a concentration of 10 to 30 mmol/liter, usually about 15 mmol/liter.

In view of the current situation as mentioned above, the present inventors have made intensive investigations to develop a particularly advantageous process from the standpoint of industry with respect to the separation of elements by chromatography in which a front zone and a rear zone are present in front of and in rear of the adsorption band of elements to be separated, respectively. For realizing such a process, the present inventors have particularly tried to develop an adsorption band of elements to be separated using an eluent having a high concentration without causing precipitation of the eluent in the column which is one of the most serious disadvantages in the conventional methods. As a result, the present inventors have found that the above-mentioned disadvantages of conventional methods can be eliminated by developing the adsorption band of elements while allowing the main eluent not to enter into the front zone which is present in front of the adsorption band of elements to be separated. Also, the present inventors have found that, by such a novel process, a mixture of elements can be separated into individual species not only in a high state of purity but also in a high state of concentration and that a greatly improved column efficiency can be achieved. The present invention has been completed based on such novel findings.

Accordingly, it is an object of the present invention to provide a process for the separation of elements by chromatography in which a front zone and a rear zone are present in front of and in rear of an adsorption band of elements to be separated, by which a mixture of elements can be separated into individual species not only in a high state of purity but also in a high state of concentration and a greatly improved column efficiency can be achieved.

According to the present invention, there is provided a process for the separation of elements by chromatography which comprises developing an adsorption band of elements to be separated without causing the entry of a main eluent into a front zone which is present in front of the adsorption band of elements to be separated.

According to the present invention, a solution of a mixture of elements is fed to a column packed with an adsorbent to form an adsorption band of elements to be separated and then the formed adsorption band is developed using a main eluent without causing the entry of the main eluent into the front zone which is present in front of the adsorption band of elements to be separated. It is preferred in the present invention that a ligand be contained in the main eluent. As such a ligand, various kinds of substances may be employed as will be described later. However, a ligand which is neutral or anionic may preferably employed in the present invention. As such a preferred ligand, a ligand having both amino group and carboxyl group may be mentioned. Among ligands having both amino group and carboxyl group, EDTA is most preferably employed in the present invention. With respect to the concentration of a ligand contained in the main eluent, 10 to 1,000 mmol/-liter is preferable. According to the present invention, it is preferred that a releasing agent for elements to be separated be contained in the main eluent and a retaining agent is present in the front zone. The term "releasing agent" as used herein is intended to mean an ion of which the ability of forming a complex compound with a ligand is low as compared with that of elements to be separated. The term "retaining agent" as used herein is intended to mean an ion of which the ability of forming a complex compound with a ligand is high as compared with that of elements to be separated. As such a releasing agent of elements, there may be employed any ion of which the ability of forming a complex compound with a ligand is low as compared with that of elements to be separated. As the retaining agent, as will be described later, there may be employed various kinds of ions of which the ability of forming complex compounds with a ligand is high as compared with that of elements to be separated. But it is preferred in the present invention that at least one ion selected from the group consisting of hydrogen ion and transition metal ions be employed as the retaining agent.

Elements which may be separated in the present invention are any of those which can be present in an aqueous solution in the form of ions. Particularly, the present invention is suitable for separating a mixture of rare earth elements.

According to the present invention, it is preferred that an adsorption band of elements to be separated is formed 50% to below 100% of the entire length of the adsorbent packed in the column and then a main eluent is fed to the column for developing the adsorption band. Even when the length of the adsorption band of elements is less than 50% of the entire length of the adsorbent packed in the column, the main eluent can be employed to elute elements if the adsorption band is migrated to a certain extent using an eluent having the same concentration as that of an eluent conventionally employed. However, in this case, a sufficiently improved column efficiency cannot be achieved, and no significant difference in column efficiency is observed between the above case and the conventional methods. When the length of an adsorption band of elements to be separated is 100% or more, the separation productivity of elements is reduced (wherein 100% or more means either a state that an adsorption band of elements to be separated is formed on the entire adsorbent in the column or a state that a solution of a mixture of elements to be separated is further fed to the column even after an element is found in the eluate from the column). To achieve a satisfactory development of the adsorption band of elements into individual bands without causing the entry of the main eluent into the front zone, it is preferred that when the length of the front zone becomes $$\frac{V}{A} \times \frac{R}{1-R} \text{ (cm) or less}$$

wherein V is the void volume of the column which includes the pore volume of the adsorbent packed in the column, cm³; A is the sectional area of the column, cm²; and R is the molar fraction of the elements to be separated which is present in the liquid phase of the adsorption band, the main eluent is fed to the column.

$$\frac{V}{A} \times \frac{R}{1-R} \text{ (cm)}$$

represents a distance from the front end of the adsorption band of elements to the bottom of the adsorbent packed in the column. That is to say, if the length of the front zone is $$\frac{V}{A} \times \frac{R}{1-R} \text{ (cm) or less}$$

in developing the adsorption band using a main eluent, the development can be carried out without causing the entry of the main eluent into the front zone.

With respect to an adsorbent to be employed in the present invention, an adsorbent having a diffusion coefficient of $5 \times 10^{-9}$ cm²/sec or more is preferably employed from viewpoints of separability and productivity. The diffusion coefficient as used herein is defined by the following equation:

$$D = -\frac{\ln(1-f^2)a^2}{4\pi^2 t}$$

wherein D is the diffusion coefficient, cm²/sec; f is the exchange ratio of Pr to Nd at 25° C.; a is the average particle diameter of the adsorbent, cm; and t is the time required for the exchange ratio (f) to reach 0.5, sec which is determined by the procedures comprising adding the adsorbent into a 100 mmol/liter Nd aqueous solution having a pH value of 6, allowing the resulting mixture to stand until the adsorbent is equilibrated with Nd and then contacting the equilibrated adsorbent with a 100 mmol/liter Pr aqueous solution until 50% of Nd adsorbed on the adsorbent is replaced by Pr. In case the adsorbent having a diffusion coefficient of less than $5 \times 10^{-9}$ cm²/sec is employed, the separability of elements is extremely lowered. Furthermore, when the adsorption band of elements to be separated is formed 50% or more of the entire length of such a adsorbent packed in a column and then the elements are subjected to elution, the productivity of separated elements is poor even if the adsorption band of elements to be separated is developed without causing the entry of the main eluent into the front zone.

According to the present invention, ion exchangers are preferably employed as the adsorbent. Both a cation exchanger and an anion exchanger may be employed in the present invention as will be described in more detail later. With respect to the cation exchanger, a cation exchanger having a micro-void volume ratio of 0.50 to 0.88 and a degree of crosslinking of 17 to 80 is preferred. The micro-void volume ratio of a cation exchanger is defined by the equation:

$$Rv = \frac{Pv}{Sv}$$

wherein Sv is the volume of the cation exchanger, and Pv is the pore volume within the cation exchanger particles.

The Pv and Sv are measured as follows;

Measurement of Pv:

(1) An aqueous solution containing 0.1 mol/liter of hydrogen ion and 0.1 mol/liter of $PrCl_3$ is supplied to a cation exchanger and the cation exchanger is equilibrated with the aqueous solution.

(2) The equilibrated cation exchanger as obtained in (1) is dehydrated by centrifugal force until the integrated amount of dehydration in the first stage becomes constant as the centrifugal force or the number of revolutions of a dehydrating machine is increased. Generally this centrifugal force corresponds to about 500 to 9,000 rpm.

(3) The water of the cation exchanger after the dehydration in (2) is evaporated in a vacuum drier.

(4) The amount of water evaporated in (3) is that of water within pores and designates the pore volume Pv within the cation exchanger particles.

Measurement of Sv:

The true volume of the dried cation exchanger is measured in an apparatus which is free from moisture. Sv is a total volume of this true volume and the pore volume Pv within the cation exchanger particles.

The term "degree of crosslinking" as used herein is represented by the following equation;

$$\text{Degree of crosslinking} = \frac{\text{Weight of crosslinkable monomer}}{\text{Total weight of crosslinkable monomer and other monomers for preparing crosslinked polymer}} \times 100.$$

When the micro-void volume ratio is less than 0.50, the diffusion coefficient decreases. Therefore, the use of such a cation exchanger as the adsorbent results in a poor separability. When the micro-void volume ratio is higher than 0.88, not only the adsorption amount of elements is rapidly reduced but also the mechanical strength of the cation exchanger becomes poor. Therefore, such an ion exchanger is not suitable for practical use. On the other hand, a cation exchanger having a micro-void volume ratio of 0.55 to 0.88 is advantageously employed in the present invention because the ion exchange rate is high even if the cation exchanger has a high degree of crosslinking. Therefore, when a cation exchanger having a micro-void volume ratio of 0.55 to 0.88 and a degree of crosslinking of 17 to 80 is employed as the adsorbent, there are such advantages that the change in volume of the ion exchanger is small during the development of the adsorption band and during the regeneration of the ion exchanger, that the pressure drop is small and that the high separation efficiency can be maintained. When the degree of crosslinking of a cation exchanger employed as the adsorbent is greater than 80, the adsorption amounts of elements is too small to use the cation exchanger for practical purposes. Therefore, a preferred degree of crosslinking of a cation exchanger is 17 to 80. From a viewpoint of mechanical strength, the more preferred degree of crosslinking of a cation exchanger is 17 to 40.

As mentioned above, any metal elements which can be present in aqueous solution in the form of ions may be separated according to the present invention. Particularly when the process of the invention is used for the separation of elements having a mutual separation factor of 0.004 or more, the separation may be carried out very effectively. Where the mutual separation factor of elements to be separated is less than 0.004, the sufficient separation cannot be achieved. Therefore, the process of the present invention cannot advantageously be employed for separating isotopes or the like which have a mutual separation factor of less than 0.004.

According to the present invention, when an adsorption band of elements to be separated is formed 50% to 80% of the entire length of an adsorbent packed in the column and separation of the elements into individual species is conducted, it is preferred that the adsorption band of elements to be separated is migrated employing an eluent having the same concentration as that of the eluent which has been employed in the conventional methods (hereinafter referred to as "preliminary eluent") until the length of the front zone becomes $$\frac{V}{A} \times \frac{R}{1-R} \text{ (cm) or less}$$

wherein V, A and R are as defined above and then the main eluent is fed to the column. In this case, it is preferred that both the preliminary eluent and the main eluent contain a ligand capable of forming complex compounds with elements to be separated. The presence of a ligand in both the eluents is effective for efficient separation between elements to be separated during the development of the adsorption band of elements. The ligand contained in the preliminary eluent is generally employed in a concentration of 0.1 to 30 mmol/liter. With respect to the concentration of a ligand contained in the main eluent, a higher concentration than in the preliminary eluent is employed and the preferred concentration is 10 to 1,000 mmol/liter. As the ligand to be contained in the main eluent, a ligand having both amino group and carboxyl group is preferably employed, and EDTA is more preferably employed as mentioned above. The ligand contained in the preliminary eluent may differ from the ligand contained in the main eluent. However, from the standpoint of easiness of the recovery, it is preferred that the same ligand as in the main eluent be employed in the preliminary eluent.

When the adsorption band of elements to be separated is formed 80% to below 100% of the entire length of an adsorbent packed in the column and separation of the elements into individual species is conducted, it is possible to employ a main eluent having a high concentration to elute elements without using a preliminary eluent. In this case, not only the process is simple but also a high productivity can be achieved. However, even though the adsorption band of elements to be separated is formed 80% to below 100% of the entire length of the adsorbent packed in a column, if the length of the front zone does not become $$\frac{V}{A} \times \frac{R}{1-R} \text{ (cm) or less}$$

wherein V, A and R are as defined above, it is preferred that the main eluent be fed to the column after the adsorption band of elements is migrated employing a preliminary eluent until the length of the front zone becomes $$\frac{V}{A} \times \frac{R}{1-R} \text{ (cm) or less}$$

wherein V, A and R as defined above. Also in this case, it is preferred that the main eluent contain a ligand having a concentration of 10 to 1,000 mmol/liter. When a preliminary eluent is employed, it is preferred that the preliminary eluent also contains a ligand in a concentration of 0.1 to 30 mmol/liter. With respect to the ligands to be contained in the main eluent and the preliminary eluent, there may preferably be employed those having both amino group and carboxyl group, more preferably EDTA.

When the adsorption band of elements is formed 80% to below 100% of the entire length of an adsorbent packed in a column, it is required that the aqueous solution containing a mixture of elements to be separated additionally contains a ligand. While, when the adsorption band of elements to be separated is formed 50% to 80% it is not necessarily required that the aqueous solution containing a mixture of elements to be separated contains a ligand. However, more effective separation of the elements can be achieved when a ligand is contained in the aqueous solution of a mixture of elements.

As described, according to the present invention, it is possible to separate a mixture of elements into individual species in a high state of purity employing a remarkably short column packed with an adsorbent, so that an extremely improved column efficiency can be achieved. Furthermore, according to the present invention, the amount of eluate is remarkably small as compared with that in the conventional methods because the separated elements can be collected as fractions in a high stage of concentration, so that the separation of elements can be carried out on a commercial scale employing a simple equipment. In addition to the above-mentioned advantages, according to the present invention, the separated elements can be efficiently precipitated from the collected fractions due to the high concentrations thereof, and the filtration and rinsing of the resulting precipitates can also be carried out efficiently.

The process of the present invention will be described in more detail below.

A typical example of the chromatographical development process of the present invention includes the following steps.

(1) A retaining agent solution is fed to a column packed with an adsorbent having a diffusion coefficient of $5 \times 10^{-9}$ cm$^2$/sec or more in order to convert the adsorbent to the retaining agent form.

(2) An aqueous solution containing a mixture of elements to be separated and a ligand (hereinafter often referred to as "original solution") is fed to the column to form an adsorption band of elements 50% to below 100% of the entire length of the adsorbent packed in the column.

(3) An aqueous solution containing a ligand in a concentration of 0.1 to 30 mmol/liter (preliminary eluent) is fed to the column to migrate the adsorption band until the length of the front zone becomes $$\frac{V}{A} \times \frac{R}{1-R} \text{ (cm)}$$

wherein V, A and R are as defined above.

(4) An aqueous solution (main eluent) containing a ligand in a higher concentration than in the preliminary eluent is then fed to the column so that the elution of the elements is continued. The effluent from the bottom of the column is collected as separate fractions.

In the step (2) mentioned above, "percent" used in connection with the formation of the adsorption band of elements is defined as follows: zero percent means a state where the original solution is not yet fed to the column (a state that the regeneration of the adsorbent has been completed); 80 percent means that the adsorption band of elements to be separated is formed 80% of the entire length of the adsorbent, from its upper end, packed in a column; 100 percent means that an adsorption band of elements to be separated is formed over the entire length of the adsorbent packed in the column; and more than 100 percent means a state that the aqueous solution of a mixture of elements to be separated is further led to the top of the column after the element to be separated is found in the effluent from the bottom of the column.

As mentioned above, the regeneration of the adsorbent is conducted in the step (1). An adsorption band of elements to be separated is formed in the step (2). The formed adsorption band of elements is migrated in the step (3). The adsorption band of elements is further developed in the step (4). In practicing the present invention, it is particularly important that the adsorption band of elements to be separated should be formed 50% to below 100% in the step (2) and that the development of the adsorption band of elements by feeding a main eluent having a high concentration of a ligand should be carried out after the length of the front zone has become $$\frac{V}{A} \times \frac{R}{1-R} \text{ (cm) or less}$$

in the steps (3) and (4). When the elution with the main eluent is conducted before the front zone becomes $$\frac{V}{A} \times \frac{R}{1-R} \text{ (cm) or less,}$$

the ligand precipitates in the column, so that the separation of elements cannot be accomplished. When the length of adsorption band of elements is less than 50%, the amount of the original solution capable of being treated per hour and the production of elements per hour cannot be improved. When the length of the adsorption band is more than 100%, the separation efficiency is remarkably lowered. Therefore, according to the present invention, the length of the adsorption band is preferably 50% to below 100%. In general, between in the case of 50% to 80% and in the case of 80% to below 100%, the manner of practice may be varied as mentioned before. When the length of the adsorption band is 80% to below 100%, the separation of elements according to the present invention can be conducted most effectively and the productivity is several times or more that of the conventional methods.

The length of the column packed with an adsorbent is not critical, but it may generally be 50 cm to 50 m, preferably 1 to 15 m. In case where the length of the column is less than 50 cm, the efficiency of obtaining pure elements is not so good. The upper limit of the length of the column is determined by taking into consideration the pressure resistance of a pump, materials, etc. employed because the use of too long a column packed with an adsorbent leads to an increase in pressure loss.

With respect to the ligand to be contained in the preliminary eluent and the main eluent, those having both amino group and carboxyl group are preferably employed, and EDTA is more preferably employed as mentioned above. Among the ligands having both amino group and carboxyl group, EDTA not only is particularly excellent in separating capacity for all the elements to be separated in the present invention but also is extremely easily recovered from the eluate because the solubility is greatly changed as the pH value of the eluate is changed. As described above, the preferred concentration of the ligand contained in the preliminary eluent is 0.1 to 30 mmol/liter. Meanwhile, the lower limit of the concentration of the ligand contained in the main eluent is determined according to the separating capacity of the ligand for the elements, and the upper limit varies depending on the types of elements to be separated, ligands, etc and generally determined by the solubility of ligands employed. However, in general, the ligand concentration of the main eluent may be 10 to 1,000 mmol/liter.

Any of those elements which are able to be present in an aqueous solution in the form of ions may be separated by the process of the present invention. When the ions of elements to be separated are cations, a cation exchanger is employed, while when the ions of elements to be separated are anions, an anion exchanger is employed. Examples of the elements which may be separated by the process of the present invention include, e.g., Li, Be, Na, Mg, Al, Si, K, Ca, Sc, Ti, V, Cr, Mn, Fe, Co, Ni, Cu, Zn, Ga, Ge, Rb, Sr, Y, Zr, Nb, Mo, Tc, Ru, Rh, Pb, Ag, Cd, In, Sn, Sb, Te, Cs, Ba, lanthanide elements, Hf, Ta, W, Re, Os, Ir, Pt, Au, Hg, Tl, Pb, Bi, Po, Fr, Ra and actinide elements. As the metal ions which can be separated, with improved productivity, by the process according to the present invention, there may be mentioned elements belonging to IIIB, IVB, VB and IIIA of the periodic table. The present invention is particularly advantageous for separating rare earth elements which have conventionally been separated with great difficulty. Among rare earth elements, the separation of lanthanide elements according to the present invention is extremely superior in separability and productivity to that of the conventional methods.

The present invention will be further explained below, particularly in connection with the separation of rare earth elements.

The term "rare earth elements" as used in the present invention include the lanthanide elements, i.e., lanthanum, cerium, praseodymium, neodymium, promethium, samarium, europium, gadolinium, terbium, dysprosium, holminum, erbium, thulium, ytterbium and lutecium; and scandium and yttrium.

Rare earth elements to be separated in the present invention each may be employed in the form of a single kind of salt thereof, such as a salt of $Cl^-$, $SO_4^{2-}$, $NO_3^-$ or $ClO_3^-$ or a mixture thereof. Any other salts than the above-mentioned may be employed insofar as they are soluble in water.

Examples of the ligand which may be employed in the present invention include citric acid, tartaric acid, oxalic acid, acetate, hydrochloric acid, sulfuric acid, polycarboxylic acid, rhodanate, cyanide, ammonia, etc. For the separation of rare earth elements, preferred ligands which can form an effective coordination compound include aminopolyacetic acids such as EDTA,1,2-diaminocyclohexanetetraacetic acid (hereinafter referred to as DCTA), N-hydroxyethylethylenediaminetriacetic acid, ethylene glycol-bis(2-aminoethyl)ether-N,N,N',N'-tetraacetic acid, diethylenetriaminepentaacetic acid, bis(2-aminoethyl)ether-N,N,N',N'-tetraacetic acid, nitrilotriacetic acid and iminodiacetic acid, and oxycarboxylic acids such as citric acid, lactic acid, glycolic acid, malic acid and tartaric acid. Of these ligands, aminopolyacetic acids have an excellent ability of separating rare earth elements. Particularly, EDTA has an excellent ability capable of separating effectively any rare earth elements.

The pH of the aqueous solution of a mixture of rare earth elements containing a ligand is preferably adjusted in such a manner that rare earth elements in the form of ions do not form a precipitate by hydrolysis and that the rare earth elements form complexes with the ligand. The preferred pH value of the aqueous solution of a mixture of rare earth elements containing a ligand is determined by the dissociation constant of the ligand employed. For example, when EDTA is used as the ligand, the preferred pH value is 2 to 4. However, the pH value is generally 0.1 to 10, preferably 1 to 6.

The pH value of a retaining agent solution is preferably adjusted in such a manner that the retaining agent does not form a precipitate by hydrolysis and the retaining agent does not lose adsorbability to the cation exchanger. For example, when Cu(II) ion is used as the retaining agent, the pH value of the retaining agent solution is preferably 0.1 to 6.9, more preferably 1 to 4. When hydrogen ion is employed as the retaining agent, the concentration of hydrogen ion is preferably at least 0.01 mol/liter, more preferably 0.1 to 5 mol/liter.

Retaining agents which may be employed alone or in combination in the present invention include $Li^+$, $H^+$, $Na^+$, $NH_4^+$, $K^+$, $Pb^+$, $UO_2^{2+}$, $Mg^{2+}$, $Zn^{2+}$, $Cd^{2+}$, $Mh^{2+}$, $Be^{2+}$, $Ca^{2+}$, $Sr^{2+}$, $Pb^{2+}$, $Ba^{2+}$, transition metal ions and the like. Among them, preferred retaining agents are at least one member selected from the group consisting of $H^+$ and transition metal ions. The retaining agents which may be preferably employed for separating rare earth elements are those which have a greater ability of forming complex compounds with a ligand than that of rare earth elements. As such retaining agents, there may be mentioned, for example, $Pb^{2+}$, $Pd^{2+}$, $Ni^{2+}$, $Cu^{2+}$, $Hf^{4+}$, $Zr^{4+}$, $Ga^{3+}$, $Ti^{3+}$, $In^{3+}$, $Fe^{3+}$, $V^{3+}$, $H^+$ (hydrogen ion) and the like. If elements having an ultra-high purity are intended to obtain, $H^+$ is preferably employed as the retaining agent.

It is necessary to adjust the pH value of the preliminary eluent for migrating an adsorption band of rare earth elements and the main eluent for eluting the rare earth elements in such a manner that, when the ligand is contacted with rare earth element ions, the formation of complex compounds between the rare earth element ions and the ligand proceeds without being accompanied by precipitation of the rare earth elements due to the hydrolysis of the rare earth element ions and that the adsorbability of the rare earth element ions to the cation exchanger is reduced. Generally, the pH of the ligand solution is adjusted so that the dissociation of the ligand may proceed. For example, when EDTA is employed as the ligand, the pH value is generally 4 to 11, preferably 5 to 10.

Acids or alkalis are employed in the regeneration of cation exchangers and the control of the pH of solutions. The acids and alkalis which can be employed in this invention include inorganic acids such as hydrochloric acid, sulfuric acid, nitric acid, perchloric acid, hydrobromic acid and any mixture thereof; and alkalis such as sodium hydroxide, potassium hydroxide, lithium hydroxide, calcium hydroxide, magnesium hydroxide, barium hydroxide, sodium carbonate, potassium carbonate, lithium carbonate, aqueous ammonia, and mixtures thereof. Of these acids and alkalis, sulfuric acid and hydrochloric acid as the acid and aqueous ammonia as the alkali are preferably employed because these substances can be burnt out by burning treatment for obtaining a finally purified product.

The separation of elements according to the present invention may be preferably conducted at a temperature ranging from $-10°$ to $150°$ C. The optimum temperature varies depending on the types of retaining agents and ligands employed and other factors. For example, when $H^+$ is employed as the retaining agent and EDTA or DCTA is employed as the ligand, the temperature is preferably 70° to 150° C. and more preferably 85° to 120° C. When Fe(III) ion is used as the retaining agent and EDTA is used as the ligand, a preferred temperature ranges from 10° to 60° C. However, the separation of elements according to the present invention may be preferably conducted at a temperature of 10° to 120° C.

As an adsorbent which can be employed in the present invention is either cation exchangers or anion exchangers as mentioned above can be utilized.

The cation exchangers which can be employed for separating rare earth elements according to the present invention may be classified as follows.

Group (1): Ion exchangers prepared by polymerization or copolymerization of monomers having a vinyl group(s), the monomers containing at least 4% by weight of a crosslinkable monomer based on the total weight of the monomers. Preferred cation exchangers of this group are sulfonated products of a crosslinked high molecular weight polymer prepared by addition copolymerization using styrene, vinylketone, divinylbenzene, etc. as the main monomer components; sulfonated products of an addition polymer containing, as the main monomer components, a monomer having an active group such as halomethylstyrene, methylvinylketone, epoxybutadiene, and acrylamide, and a crosslinkable monomer such as divinylbenzene, triallyl isocyanurate; polymers prepared by copolymerization of a crosslinkable monomer and a monomer having a functional group capable of becoming an ion exchange group such as sodium vinylsulfonate, methacrylic acid and acrylic acid, and alkylesters thereof and phenylesters thereof; and the like.

The monomers which can be employed in preparing the skeleton of cation exchangers include styrene and styrene derivatives such as methylstyrene, ethylstyrene, vinylnaphthalene, 3,4,6-trimethylstyrene, chlorostyrene, methoxystyrene, N,N-dimethylaminostyrene, nitrostyrene, chloromethylstyrene, trifluorostyrene, trifluoromethylstyrene and aminostyrene; butadiene; acrylonitrile derivatives; acrylic acid and acrylic esters such as methyl acrylate and chloromethyl acrylate; methacrylic acid and methacrylic esters such as cyclohexyl methacrylate, dimethylaminoethyl methacrylate, glycidyl methacrylate and methyl methacrylate; diethyl maleate; diethyl fumarate; vinyl ketones such as methyl vinyl ketone and ethyl isopropyl ketone; vinylidenes; acrylamide derivatives; aliphatic acid vinyl esters such as vinyl acetate, vinyl butylate and vinyl caprate; epoxybutadiene; and sulfur-containing compounds such as vinylsulfonic acid ethyl ester, vinylsulfonic acid phenyl ester, styrenesulfonic acid, styrenesulfonates, styrenesulfonic acid butyl ester, and methylvinyl sulfide.

The crosslinkable monomers which can be employed in preparing the skeleton of cation exchangers include divinylbenzene, divinyltoluene, divinylnaphthalene, divinylethylbenzene, trivinylbenzene, divinyldiphenylmethane, divinylbenzyl, divinylsulfone, divinylketone, bis(vinylpyridinoethyl)ethylenediamine, diallyl phthalate, triallylamine, N,N'-ethylenediacrylamide, ethylene glycol dimethacrylate, triethylene glycol dimethacrylate, trimethylpropane triacrylate, triallyl isocyanurate and diallyl melamine.

Preferred cation exchangers are sulfonated products of a crosslinked high molecular weight polymer prepared by addition copolymerization of styrene, vinyltoluene and ethylbenzene with divinylbenzene as the main monomer components; sulfonated products of a crosslinked polymer prepared by addition copolymerization of, as the main monomer components, a monomer having an active group such as chloromethylstyrene, methylethyl ketone, epoxybutadiene and acrylamide with a crosslinkable monomer such as divinylbenzene or triallyl cyanurate; polymers prepared by polymerization of, as the main monomer component, a monomer having a sulfur atom capable of becoming an ion exchange group such as vinylsulfonic acid phenyl ester, styrenesulfonate, styrenesulfonic acid butyl ester and methylvinyl sulfide, or, if desired, by copolymerization of such a monomer with a crosslinkable monomer; a condensation polymer of phenolsulfonic acid with formaldehyde; and the like. The cation exchanger having a structure or performance particularly suitable for the present invention can be easily prepared from styrene-divinylbenzene copolymers as the starting materials.

One of the preferred methods of producing particles of the cation exchange resins is a suspension polymerization method. In conducting the addition polymerization or the condensation polymerization of oil-soluble monomers, it is preferred to employ an oil-in-water suspension. In this case, particles having a narrow particle distribution can be obtained by selecting appropriate conditions. Meanwhile, in conducting the addition polymerization or the condensation polymerization of water-soluble monomers, it is necessary to employ water-in-oil suspension. It is more difficult to obtain the water-in-oil suspension technically than to obtain the oil-in-water suspension. However, if it is possible to prepare suspension-water droplets, particles having a comparatively narrow particle distribution can be obtained.

In the case of using oil-soluble monomers, the suspension may preferably contain a viscous substance such as gum arabic, gamboge, rosin, pectin, an alginate, tragacanth gum, agar, methyl cellulose, starch, carboxymethyl cellulose, karaya gum, and gelatin; a synthetic high molecular weight substance such as sodium polyacrylate, polyvinyl alcohol, polyvinyl pyrrolidone and diacetoolein; and an inorganic substance such as magnesium aluminum silicate, hydrated magnesium silicate, titanium oxide, zinc oxide, calcium carbonate, talc, barium sulfate, calcium phosphate, aluminum hydroxide and silicic acid anhydride, and, if necessary, the suspension may preferably contain a salt such as sodium chloride, a pH controlling agent and an emulsifier. In suspending water in oil, it is preferred to employ a surfactant together with a suspending agent comprising a synthetic high molecular weight substance. Particularly preferable surfactants include sorbitan esters, sorbitan ester ethers, fatty acid soap and fatty acid glycerides.

Group (2): Ion exchangers in which an ion exchangeable substance is supported on an organic carrier. As such an organic carrier, there may be employed high molecular weight polymers such as polyethylene, polypropylene, polystyrene and styrene-divinylbenzene copolymer. Preferred cation exchangers can be prepared by supporting a cation exchangeable substance on an organic carrier by means of adsorption, reaction or graft polymerization, or by providing the surface of an organic carrier with the ability to exchange ions by means of reaction. A preferable example of these cation exchangers is a cation exchanger obtained by sulfonating a styrene-divinylbenzene copolymer.

Group (3): Ion exchangers in which an ion exchangeable substance is supported on an inorganic carrier. Preferable inorganic carriers include carbon, silica gel, zeolite, activated clay, glass beads, and the like. The cation exchanger can be prepared by supporting an ion exchangeable substance by means of adsorption, reaction, graft copolymerization, etc. This type of ion exchangers is widely used in a specific field of analytical chemistry. The ion exchangers whose carriers are glass beads and other known carriers as described in Japanese Patent Application Laid-Open No. 32085/1975, and the ion exchangers whose carriers are silica gel and other known carriers as described in Japanese Patent Publication No. 18255/1981 are advantageously used in the present invention.

Of the above-mentioned cation exchangers, cation exchangers having a sulfone group may preferably be employed for separating rare earth elements. The object of the present invention can be effectively achieved by using such exchangers because of the excellent performance thereof. According to the present invention, it is preferred that the micro-void volume ratio of the cation exchanger is 0.5 to 0.88. When the micro-void volume ratio is less than 0.5, the diffusion coefficient of the cation exchanger is small, so that a sufficient separation efficiency cannot be accomplished. When the micro-void volume ratio is higher than 0.95, the adsorption amount of elements is remarkably reduced, which results in a poor separation efficiency.

The anion exchangers which may be employed in the present invention are those having ion exchange groups such as $----N^+X^-$, $----P^+$ and $---S^+$. Such anion exchangers may be prepared, for example, by chloromethylating a copolymer bead of styrene and divinylbenzene with chloromethyl ether in the presence of a Lewis acid catalyst such as $AlCl_3$ and then reacting the chloromethylated copolymer bead with a tertiary amine; by reacting a copolymer bead of ethyl acrylate and divinylbenzene with a polyamine such as N,N-dimethylaminopropylamine to introduce amino groups into such a copolymer bead; by condensation between m-phenylenediamine and formaline; and by reacting polyethyleneimine with epichlorohydrin. When an anion exchanger is employed as the adsorbent in the present invention, preferred retaining agents are anions such as $I^-$, $C_6H_5O^-$, $HSO_4^-$, $NO_3^-$, $Br^-$, $CN^-$, $HSO_3^-$, $NO_2^-$, $Cl^-$, $HCO_3^-$, $H_2PO_4^-$, $HCOO^-$, $CH_3COO^-$, $OH^-$ and $F^-$.

The present invention will be illustrated in more detail with reference to the following Examples, which should not be construed to be limiting the scope of the present invention.

EXAMPLE 1

An ion exchange column equipped with a filter at the bottom thereof and having an inside diameter of 2.0 cm and a length of 2.5 m was packed with a cation exchange resin, a sulfonated product of a styrene-divinylbenzene copolymer, having a microvoid volume ratio of 0.72, a degree of crosslinking of 25, an average particle diameter of 120$\mu$ and a diffusion coefficient of $5 \times 10^{-6}$ cm$^2$/sec. Then the temperature of the whole column was maintained at 90° C., and to the top of the column was supplied 0.5 N $H_2SO_4$ at a rate of 140 ml per minute for about 15 minutes to convert the entire resin to its hydrogen ion form. An aqueous solution (original solution) containing 1.525 g/liter of $Y_2(SO_4)_3.8H_2O$ (5 mmol/liter of Y), 1.832 g/liter of $Sm_2(SO_4)_3.8H_2O$ (5 mmol/liter of Sm), 1.667 g/liter of $Nd_2(SO_4)_3.5H_2O$ (5 mmol/liter of Nd), 4.384 g/liter of EDTA (15 mmol/liter of EDTA) and 0.001 g/liter of hydrogen ion was supplied to the top of the column at a rate of 140 ml per minute until an adsorption band was formed 60% of the entire length of the cation exchanger, from its upper end, packed in the column. Subsequently, an aqueous solution containing 15 mmol/liter of EDTA and 45 mmol/liter of $NH_4OH$ (preliminary eluent) was fed to the top of the column at a rate of 140 ml per minute. When the length of the front zone reached 7 cm, an aqueous solution containing 40 mmol/liter of EDTA and 120 mmol/liter of $NH_4OH$ (main eluent) was fed to the top of the column at a rate of 140 ml per minute. The eluate from the bottom of the column was collected in fractions by means of a fraction collector connected to the bottom of the column.

The length of the front zone required for the elements to be eluted without causing the entry of the main eluent into the front zone was calculated from the equation $$\frac{V}{A} \times \frac{R}{1-R} \text{ (cm)}$$

wherein V, A and R are as defined above. In Example 1, since V was 588 cm$^3$, A was 3.14 cm$^2$ and R was 0.05 the length of the front zone was 9.8 cm. Therefore, if the main eluent is fed to the column when the length of the front zone reached 9.8 cm or less, the elements can be eluted without causing the entry of the main eluent into the front zone.

The concentration of the rare earth elements in respective fraction was determined by X-ray fluorescence. The yields of yttrium, samarium and neodymium each having a purity of more than 99%, were 94.7%, 90.3% and 95.6%, respectively. The amount of treatment per unit time was 2.30 mol/hr and the production of rare earth elements having a purity of more than 99% was 2.15 mol/hr.

EXAMPLE 2

Substantially the same procedures as in Example 1 were repeated except that the adsorption band was formed 90% of the entire length of the exchanger packed in the column and the preliminary eluent was not supplied to the column. The results are shown in Table 1.

EXAMPLE 3

Substantially the same procedures as in Example 1 were repeated except that an adsorption band of elements was formed just below 100% of the entire length of the exchanger packed in the column and the preliminary eluent was not supplied to the column. The results are shown in Table 1.

COMPARATIVE EXAMPLE 1

The ion exchange column employed in Example 1 was regenerated and then an aqueous solution containing 5 mmol/liter of yttrium, 5 mmol/liter of samarium and 5 mmol/liter of neodymium but not containing EDTA was supplied to the top of the column at a rate of 140 ml per minute until the adsorption band was formed 90% of the entire length of the exchanger packed in the column. Subsequently, an aqueous solution (preliminary eluent) containing 4.384 g/liter of EDTA (15 mmol/liter of EDTA) and 1.575 g/liter of $NH_4OH$ (45 mmol/liter of $NH_4OH$) was fed to the top of the column at a rate of 140 ml/min. Substantially the same procedures as in Example 1 were repeated to determine the amounts of the rare earth elements in the eluate from the bottom of the column. The results are shown in Table 1. As is apparent from Table 1, Examples 2 and 3 in which an original solution containing EDTA was used gave excellent results of separation of rare earth elements as compared with Comparative Example 1 in which an original solution not containing EDTA was used.

TABLE 1

| | Adsorption band (%) | Yield (%) (Purity > 99%) | | | Amount of treatment per unit time (mol/hour) | Production per unit time (mol/hour) |
|---|---|---|---|---|---|---|
| | | Y | Sm | Nd | | |
| Example 2 | 90 | 88.5 | 81.5 | 92.3 | 3.36 | 2.94 |
| Example 3 | just below 100 | 88.0 | 80.9 | 91.9 | 3.73 | 2.96 |
| Comparative Example 1 | 90 | 5.0 | 0 | 7.3 | 3.36 | 0.14 |

COMPARATIVE EXAMPLE 2

Substantially the same procedures as in Example 1 were repeated except that an adsorption band was formed 30% of the entire length of the exchanger packed in the column. The yields of yttrium, samarium and neodymium were 97.8%, 95.5% and 97.8%, respectively. The amount of treatment per unit time and the amount of production per unit time of rare earth elements having a purity of more than 99% were 1.6 mol/hour and 1.56 mol/hour, respectively. The amount of production was about ½ that in Example 2.

EXAMPLE 4

The length of the adsorption band was varied within the range of from 20% to 80% as indicated in Table 2, and substantially the same procedures as in Example 1 were repeated. In addition, the length of the adsorption band was varied within the range of from 85 to just below 100%, and substantially the same procedures as in Example 2 were repeated.

For the comparison of the amount of production, substantially the same procedures as in Comparative Example 1 were repeated except that the length of adsorption band was varied. The amounts of rare earth elements in the eluate from the bottom of the column were determined in the same manner as in Example 1. The results are shown in Table 2. As is apparent from Table 2, the production of rare earth elements having a purity of more than 99% according to the present invention was increased 4.8 times when the adsorption band was formed 80% of the exchanger and more than 10 times when an adsorption band was formed 85% or more of the exchanger, as compared with that of the conventional method.

TABLE 2

| | Production per unit time (mol/hr) | | | |
|---|---|---|---|---|
| Adsorption band (%) | (A) 15 mmol/liter of EDTA is contained in original solution | (B) EDTA is not contained in original solution | Difference of production (mol/hr) (A) − (B) | Ratio of production (A)/(B) |
| 20 | 1.10 | 0.95 | 0.15 | 1.2 |
| 50 | 2.20 | 1.25 | 0.95 | 1.8 |
| 75 | 2.75 | 1.10 | 1.65 | 2.5 |
| 80 | 2.85 | 0.60 | 2.25 | 4.8 |
| 85 | 2.90 | 0.20 | 2.70 | 14.5 |
| 90 | 2.94 | 0.14 | 2.80 | 21.0 |
| just below 100 | 2.96 | 0.12 | 2.84 | 24.7 |

EXAMPLE 5

An ion exchange column equipped with a filter at the bottom thereof and having an inside diameter of 2.0 cm and a length of 2.5 m was packed with a cation exchange resin, a sulfonated product of a styrene-divinylbenzene copolymer, having a micro-void volume ratio of 0.7, a degree of crosslinking of 30, an average particle diameter of 120μ and a diffusion coefficient of $6 \times 10^{-6}$ $cm^2$/sec. Then the temperature of the whole column was maintained at 90° C., and to the top of the column was supplied 0.5 N $H_2SO_4$ at a rate of 140 ml/min for about 15 minutes to convert the entire resin to its hydrogen ion form. An aqueous solution (original solution) containing 7.5 mmol/liter of Pr, 7.5 mmol/liter of Nd and 15 mmol/liter of EDTA was fed to the column until an adsorption band was formed 60% of the entire length of the exchanger packed in the column. Subsequently, an aqueous solution containing 15 mmol/liter of EDTA, 45 mmol/liter of $NH_4OH$ (preliminary eluent) was fed to the column in order to develop the adsorption band of elements. When the front end of the adsorption band of elements reached the position 16 cm above the bottom of the packed cation exchanger bed, an aqueous solution containing 100 mmol/liter of EDTA and 300 mmol/liter of $NH_4OH$ (main eluent) was supplied to the column to elute elements. The eluate from the column was collected in separate fractions by means of a fraction collector connected to the bottom of the column. Each fraction was analysed by means of X-ray fluorescence to evaluate the concentration of Pr and Nd in each fraction. Fractions containing rare earth elements having a purity of more than 99% were put together. $H_2SO_4$ was then added to the mixed fraction for adjusting the pH value to 1.5. Precipitated EDTA was filtered off. To the resulting filtrate was added $NH_4OH$ to adjust the pH value to 9. Each of Pr and Nd precipitated in the form of hydroxide was separated from the solution by filtration and dried at 110° C. for 5 hours. The results obtained are shown in Table 3.

COMPARATIVE EXAMPLE 3

Substantially the same procedures as in Example 5 were repeated except that an aqueous solution containing 100 mmol/liter of EDTA and 300 mmol/liter of NH4OH (main eluent) solution was not employed. The results obtained are shown in Table 3.

As apparent from Table 3, Example 5 in which the average molar concentration of rare earth elements in fractions was high gave a high recovery of rear earth elements in the form of hydroxides as compared with that of Comparative Example 3.

TABLE 3

|  | Average molar concentration of rare earth elements in fractions | Yield (%) (purity > 99%) | | Recovery of rare earth elements in the form of hydroxides | |
| --- | --- | --- | --- | --- | --- |
|  |  | Pr | Nd | Pr | Nd |
| Example 5 | 62 mmol/liter | 96.7% | 96.7% | 97.1% | 97.9% |
| Comparative Example 3 | 10 mmol/liter | 97.3% | 97.3% | 89.0% | 86.2% |

EXAMPLES 6 TO 8

Original solutions having varied concentration of rare earth elements and EDTA as shown in Table 4 were prepared. Each original solution was fed to the same ion exchange column as in Example 5 until the length of the adsorption band reached 70% of the entire length of the ion exchanger packed in the column. An aqueous solution containing 15 mmol/liter of EDTA and 30 mmol/liter of NH4OH (preliminary eluent) was supplied to the column until the front end of the adsorption band reached just above the bottom of the column, followed by feeding an aqueous EDTA solution having a different EDTA concentration from that of the original solution. Analysis of the eluate and recovery of the rear earth elements in the form of hydroxides were conducted in the same manner as in Example 5. The results are shown in Table 4.

COMPARATIVE EXAMPLE 4

Substantially the same procedures as in Example 6 were repeated except that an aqueous EDTA solution having the same EDTA concentration as that of the original solution was fed to the column when the front end of the adsorption band reached just above the bottom of the column. The results are shown in Table 4.

COMPARATIVE EXAMPLE 5

An original solution of the same compositions of rare earth elements as in Example 8 and 60 mmol/liter of EDTA was fed to the same exchange column as in Example 5. The ion exchanger began to form an adsorption band. However, after a while, EDTA precipitated in the column, so that the separation of rare earth elements could not be achieved.

TABLE 4

|  | Composition of original solution (mmol/liter) | | | | Concentration of EDTA in main eluent (mmol/liter)* | Average molar concentration of rare earth elements in fractions (mmol/liter) | Yield (%) (Purity > 99%) | | | Recovery of rare earth elements in the form of hydroxides (%) | | | Remarks |
| --- | --- | --- | --- | --- | --- | --- | --- | --- | --- | --- | --- | --- | --- |
|  | Y | Sm | Nd | EDTA |  |  | Y | Sm | Nd | Y | Sm | Nd |  |
| Comparative Example 4 | 5 | 5 | 5 | 15 | 15 | 10 | 97.4 | 94.6 | 97.2 | 88.3 | 89.1 | 88.4 |  |
| Example 6 | 5 | 5 | 5 | 15 | 60 | 35 | 96.9 | 92.7 | 96.9 | 97.6 | 97.1 | 97.0 |  |
| Example 7 | 10 | 10 | 10 | 30 | 100 | 61 | 93.9 | 88.7 | 94.4 | 98.1 | 97.9 | 98.0 |  |
| Comparative Example 5 | 20 | 20 | 20 | 60 | — | — | — | — | — | — | — | — | Elements could not be separated because of precipitation of EDTA |
| Example 8 | 20 | 20 | 20 | 30 | 150 | 92 | 91.6 | 85.7 | 92.3 | 99.3 | 99.3 | 99.2 |  |

Note:
*The EDTA concentration of the eluent fed after the front end of the adsorption band reached just above the bottom of the exchanger.

EXAMPLES 9 TO 11

An ion exchange column equipped with a filter at the bottom of the column and having an inside diameter of 2.0 cm and a length of 2.5 m was packed with a sulfonated product of a styrenedivinylbenzene copolymer. The whole column was maintained at 90° C. and to the top of the column was fed 0.5 N H2SO4 at a rate of 140 ml/min for 15 minutes to convert the entire resin to its hydrogen form. Subsequently, an aqueous solution (original solution) containing 1.525 g/liter of Y2(SO4)3.8H2O (5 mmol/liter of Y), 1.832 g/liter of Sm2(SO4)3.8H2O (5 mmol/liter of Sm), 1.667 g/liter of Nd2(SO4)3.5H2O (5 mmol/liter of Nd), 4.384 g/liter of EDTA (15 mmol/liter) and 0.001 g/liter of hydrogen ion was fed to the column until the adsorption band was formed 60% in Example 9, 90% in Example 10 and just below 100% in Example 11 of the entire length of the exchanger packed in the column. An aqueous solution containing 4.384 g/liter of EDTA (15 mmol/liter) and 1.575 g/liter of NH4OH (preliminary eluent) was fed to the column at a rate of 140 ml/min until the front end of the adsorption band reached just above the bottom of the exchanger. Subsequently, an aqueous solution containing 100 mmol/liter of EDTA and 300 mmol/liter of NH4OH (main eluent) was fed to the column to elute the elements. The eluate from the bottom of the column was collected in fractions by means of a fraction collector connected to the bottom of the column. The concentration of rare earth elements in each fraction was determined by X-ray fluorescence.

Fractions containing rare earth elements each having a purity of more than 99% were put together. H2SO4 was added to the mixed fraction for adjusting the pH value to 1.5. Precipitated EDTA was filtered off. To the resulting filtrate was added NH4OH to adjust the pH value to 9. The resulting precipitates of rare earth elements in the form of hydroxides each were separated from the solution by filtration and dried at 110° C. for 5 hours. The results are shown in Table 5.

TABLE 5

|  | Adsorption band (%) | Average molar concentration of rare earth elements in fractions | Recovery of rare earth elements in the form of hydroxides | Production per unit time |
| --- | --- | --- | --- | --- |
| Example 9 | 60 | 74 mmol/liter | 90% | 4.30 mol/liter |
| Example 10 | 90 | 90 mmol/liter | 93% | 5.58 mol/liter |

TABLE 5-continued

|  | Adsorption band (%) | Average molar concentration of rare earth elements in fractions | Recovery of rare earth elements in the form of hydroxides | Production per unit time |
|---|---|---|---|---|
| Example 11 | just below 100 | 95 mmol/liter | 95% | 5.63 mol/liter |

Note: In Example 11, preliminary eluent was not employed because the original solution was fed to the column until the front end of the adsorption band reached just above the bottom of the column.

EXAMPLE 12

Substantially the same procedures as in Example 9 were repeated except that the length of the adsorption band was varied as indicated in Table 6. For the comparison of production, after the ion exchange column employed in Example 9 was regenerated, an aqueous solution (original solution) containing 5 mmol/liter of Y, 5 mmol/liter of Sm and 5 mmol/liter of Nd but not containing EDTA was fed to the column until the adsorption band was formed a predetermined percent as indicated in Table 6. Subsequently, an aqueous solution containing 4.384 g/liter of EDTA (15 mmol/liter) and 1.575 g/liter of NH$_4$OH (45 mmol/liter) was fed to the column at a rate of 140 ml/min.

The eluate from the bottom of the column was analysed to evaluate the concentration of rare earth elements in the same manner as in Example 9. The results are shown in Table 6.

As apparent from Table 6, the production of rare earth elements according to the present invention was increased 9.1 times when the adsorption band was formed 80% of the entire length of the exchanger and more than 25 times when the adsorption band was formed 85% or more of the entire length of the exchanger, as compared with that of the conventional method.

TABLE 6

| Adsorption band (%) | Production per unit time (mol/hr) | | Ratio of production (A)/(B) |
|---|---|---|---|
|  | (A) 15 mmol/liter of EDTA is contained in original solution | (B) EDTA is not contained in original solution |  |
| 20 | 2.05 | 0.95 | 2.2 |
| 40 | 3.40 | 1.12 | 3.0 |
| 60 | 4.30 | 1.18 | 3.6 |
| 75 | 5.35 | 1.10 | 4.9 |
| 80 | 5.43 | 0.60 | 9.1 |
| 85 | 5.52 | 0.20 | 27.6 |
| 90 | 5.58 | 0.14 | 39.9 |
| just below 100 | 5.63 | 0.12 | 46.9 |

EXAMPLES 13 TO 15

Original solutions having varied concentration of rare earth elements and EDTA as indicated in Table 7 were prepared. Each original solution was fed to the same ion exchange column as in Example 9 until the length of the adsorption band reached 90% of the entire length of the ion exchanger packed in the column. Subsequently, the main eluent having a concentration of EDTA as indicated in Table 7 was fed to the column. Analysis of the eluate and recovery of the rear earth elements in the form of hydroxides were conducted in the same procedures as in Example 9. The results are shown in Table 7.

COMPARATIVE EXAMPLE 6

An original solution of the same composition of rare earth elements as in Example 15 and 60 mmol/liter of EDTA was fed to the same exchange column as in Example 9. The ion exchanger began to form an adsorption band. However, after a while, EDTA precipitated in the column, so that the separation of rear earth element could not be achieved. The results are shown in Table 7.

TABLE 7

|  | Composition of original solution (mmol/liter) | | | Concentration of EDTA in main eluent (mmol/liter) | Recovery of rare earth elements in the form of hydroxides (%) | Production per unit time (mol/hr) |
|---|---|---|---|---|---|---|
|  | Y | Sm | Nd | EDTA |  |  |  |
| Example 13 | 5 | 5 | 5 | 15 | 60 | 88 | 3.85 |
| Example 14 | 10 | 10 | 10 | 30 | 100 | 92 | 5.61 |
| Example 15 | 20 | 20 | 20 | 30 | 150 | 97 | 5.67 |
| Comparative Example 6 | 20 | 20 | 20 | 60 | — | Elements could not be separated because of precipitation of EDTA | |

COMPARATIVE EXAMPLE 7

Substantially the same procedures as in Example 2 were repeated except that a cation exchange resin, a sulfonated product of a styrene-divinylbenzene copolymer, having a micro-void volume ratio of 0.45, a degree of crosslinking of 12, an average particle diameter of 120$\mu$ and a diffusion coefficient of $1 \times 10^{-9}$ cm$^2$/sec was employed. As a result, the yields of Y, Sm and Nd having a purity of more than 99% were 12.0%, 0% and 14.2%, respectively. The amount of treatment per unit time was 3.36 mol/hr and the production per unit time was 0.2 mol/hr.

EXAMPLE 16

A jacketed cylindrical ion exchange column equipped with a filter at the bottom thereof and having an inside diameter of 2.0 cm and a length of 60 cm was packed with a cation exchange resin, a sulfonated product of a styrene-divinylbenzene copolymer, having a micro-void volume ratio of 0.74, a degree of crosslinking of 30, an average particle diameter of 100$\mu$ and a diffusion coefficient of $8 \times 10^{-6}$ cm$^2$/sec. Then the temperature of the whole column was maintained at 90° C. and to the top of the column was supplied 0.5 N HCl to convert the entire resin to its hydrogen ion form. An aqueous solution (original solution) containing 10 mmol/liter of EDTA, 7.5 mmol/liter of cupric chloride, 7.5 mmol/liter of nickel chloride and 30 mmol/liter of ammonium hydroxide was fed to the column until the length of an adsorption band of elements reached 85% of the entire length of the exchanger packed in the column. Subsequently, a main eluent containing 50 mmol/liter of EDTA and 175 mmol/liter of ammonium hydroxide was fed to the column. The eluate from the bottom of the column was collected in 15 ml fractions. The concentration of metal ions in each fraction was determined by X-ray fluorescence. As a result, it was found that copper was present in fractions Nos. 3 to 11 and that nickel was present in fractions Nos. 9 to 18. In fractions Nos. 3 to 8, only copper was present as a metal ion at a concentration of 40 mmol/liter. In fractions Nos. 12 to 18, only nickel was present as a metal ion at a concentration of 40 mmol/liter.

EXAMPLE 17

A jacketed cylindrical ion exchange column equipped with a filter at the bottom thereof and having an inside diameter of 2.0 cm and a length of 60 cm was packed with a cation exchange resin, a sulfonated product of a styrene-divinylbenzene copolymer, having a micro-void volume ratio of 0.78, a degree of crosslinking of 35, an average particle diameter of 120μ and a diffusion coefficient of $9 \times 10^{-6}$ cm²/sec. Then the temperature of the whole column was maintained at 90° C., and to the top of the column was supplied 0.5 N $HNO_3$ to convert the entire resin to its hydrogen ion form. Then an aqueous solution (original solution) containing 100 mmol/liter of EDTA, 7.5 mmol/liter of nickel chloride, 7.5 mmol/liter of cobalt chloride and 30 mmol/liter of ammonium hydroxide was fed to the column until the length of the adsorption band of elements reach 90% of the entire length of the ion exchanger packed in the column. Subsequently, a main eluent containing 50 mmol/liter of EDTA, 175 mmol/liter of ammonium hydroxide was fed to the column in order to develop the adsorption band of elements. With the development of the element adsorption band, the eluate from the bottom of the column was collected in 15 ml fractions. Each fraction was then analyzed to evaluate the concentration of metal ions contained in each fraction. As a result, it was found that, in fractions Nos. 2 to 8, only nickel was present as a metal ion at a concentration of 40 mmol/liter, that in fractions Nos. 8 to 12, both nickel and cobalt were present and that in fractions Nos. 13 to 18, only cobalt was present at a concentration of 40 mmol/liter.

COMPARATIVE EXAMPLE 8

Substantially the same procedures as in Example 17 were repeated except that the original solution was fed to the column until the adsorption band was formed 40% of the entire length of the exchanger packed in the column. As a result, EDTA precipitated in the column immediately on feeding of the main eluent, so that the separation of elements could not be achieved.

What is claimed is:

1. In a process for the separation of elements selected from the group consisting of Li, Be, Na, Mg, Al, Si, K, Ca, Sc, Ti, V, Cr, Mn, Fe, Co, Ni, Cu, Zn, Ga, Ge, Rb, Sr, Y, Zr, Nb, Mo, Tc, Ru, Rh, Pb, Ag, Cd, In, Sn, Sb, Te, Cs, Ba, lanthanide elements, Hf, Ta, W, Re, Os, Ir, Pt, Au, Hg, Tl, Pb, Bi, Po, Fr, Ra and actinide elements, by chromatography which comprises supplying an original aqueous solution of a mixture of elements to be separated to a column packed with an adsorbent to form an adsorption band of elements on the adsorbent while forming a front zone left in front of the adsorption band and feeding an eluent to the column to develop the adsorption band while forming a rear zone in rear of the adsorption band, the improvement wherein when the length of the front zone becomes $$\frac{V}{A} \times \frac{R}{1-R} \text{ (cm) or less}$$

wherein V is the void volume of the column which includes the pore volume of the adsorbent packed in the column, cm³; A is the sectional area of the column, cm² and R is the molar fraction of the elements to be separated which is present in the liquid phase of the adsorption band, the adsorption band of elements formed on the adsorbent packed in a column is developed using a main eluent having a relatively high concentration, whereby the adsorption band of elements is developed without causing the entry of said main eluent into the front zone.

2. A process according to claim 1, wherein the length of the adsorption band of elements is 50% to below 100% of the entire length of the adsorbent packed in the column.

3. A process according to claim 2, wherein the length of the adsorption band of elements is 50% to 80%.

4. A process according to claim 3, wherein when the length of the front zone becomes $$\frac{V}{A} \times \frac{R}{1-R} \text{ (cm) or less}$$

wherein V, A and R are as defined above, the main eluent is fed to the column.

5. A process according to claim 4, wherein a preliminary eluent is fed to the column so that the adsorption band is migrated until the length of the front zone becomes $$\frac{V}{A} \times \frac{R}{1-R} \text{ (cm) or less,}$$

said preliminary eluent and said main eluent containing a ligand capable of forming complex compounds with the elements to be separated.

6. A process according to claim 5, wherein the preliminary eluent has a ligand concentration of 0.1 to 30 mmol/liter and the main eluent has a ligand concentration of 10 to 1,000 mmol/liter.

7. A process according to claim 2, wherein the original aqueous solution of a mixture of elements to be separated contains a ligand and the length of the formed adsorption band of elements to be separated is 80% to below 100%.

8. A process according to claim 7, wherein when the length of the front zone becomes $$\frac{V}{A} \times \frac{R}{1-R} \text{ (cm) or less}$$

wherein, V, A and R are as defined above, the main eluent is fed to the column.

9. A process according to claim 8, wherein a preliminary eluent is fed to the column so that the adsorption band is migrated until the length of the front zone becomes $$\frac{V}{A} \times \frac{R}{1-R} \text{ (cm) or less}$$

wherein V, A and R are as defined above, said preliminary eluent and said main eluent containing a ligand capable of forming complex compounds with the elements to be separated.

10. A process according to claim 9, wherein the preliminary eluent has a ligand concentration of 0.1 to 30 mmol/liter and the main eluent has a ligand concentration of 10 to 1,000 mmol/liter.

11. A process according to claim 1, wherein said main eluent contains a ligand capable of forming complex compounds with the elements to be separated.

12. A process according to claim 11, wherein said main eluent has a ligand concentration of 10 to 1,000 mmol/liter.

13. A process according to claim 11, wherein said main eluent contains a releasing agent for the elements to be separated, and a retaining agent for the elements to be separated is present in the front zone, said releasing agent being an ion which is low in ability of forming a complex compound with the ligand relative to that of the elements to be separated, said retaining agent being an ion which is high in ability of forming a complex compound with the ligand relative to that of the elements to be separated.

14. A process according to claim 11, wherein said ligand contains both amino group and carboxyl group.

15. A process according to claim 14, wherein said ligand is ethylenediaminetetraacetic acid.

16. A process according to claim 13, wherein said retaining agent is at least one ion selected from the group consisting of hydrogen ion and transition metal ions.

17. A process according to claim 11, wherein said ligand is neutral or anionic and said adsorbent of elements to be separated is a cation exchanger.

18. A process according to claim 17, wherein said elements to be separated are rare earth elements and said ligand contains both amino group and carboxyl group.

19. A process according to claim 2, wherein said adsorbent has a diffusion coefficient of $5 \times 10^{-9}$ cm$^2$/sec or more, said diffusion coefficient being defined by the following equation:

$$D = -\frac{\ln(1 - f^2)a^2}{4\pi^2 t}$$

wherein D is the diffusion coefficient, cm$^2$/sec; f is the exchange ratio of Pr to Nd at 25° C.; a is the average radius of particles of adsorbent, cm; and t is the time required for the exchange ratio (f) to reach 0.5, sec which is determined by adding an adsorbent into a 100 mmol/liter Nd solution having a pH value of 6, allowing the resulting mixture to stand until the adsorbent is equilibrated with Nd and then contacting the equilibrated adsorbent with a 100 mmol/liter Pr aqueous solution until 50% of Nd adsorbed on the adsorbent is replaced by Pr.

20. A process according to claim 19, wherein said adsorbent is a cation exchanger having a micro-void volume ratio of 0.50 to 0.88 and a degree of crosslinking of 17 to 80.

21. A process according to claim 2, wherein said elements to be separated have a mutual separation factor of at least 0.004.

* * * * *